US006265596B1

(12) United States Patent
Härröd et al.

(10) Patent No.: US 6,265,596 B1
(45) Date of Patent: Jul. 24, 2001

(54) PARTIALLY HYDROGENATED FATTY SUBSTANCES WITH A LOW CONTENT OF TRANS FATTY ACIDS

(75) Inventors: Magnus Härröd, Alingsås (SE); Poul Möller, Århus (DK)

(73) Assignee: Poul Moller Ledelses - og Ingeniorradgivning APS, Arhus C (DK)

( * ) Notice: Subject to any disclaimer, the term of this patent is extended or adjusted under 35 U.S.C. 154(b) by 0 days.

(21) Appl. No.: 09/262,185

(22) Filed: Mar. 4, 1999

Related U.S. Application Data

(63) Continuation-in-part of application No. 08/765,622, filed as application No. PCT/SE95/00824 on Jul. 3, 1995, now Pat. No. 5,962,711.

(51) Int. Cl.[7] .......... C07C 57/00
(52) U.S. Cl. .......... 554/223
(58) Field of Search .......... 554/223

(56) References Cited

U.S. PATENT DOCUMENTS 3,969,382 7/1976 Zosel .

FOREIGN PATENT DOCUMENTS 4405029 8/1995 (DE) .
94/06738 3/1994 (WO) .
9406738 3/1994 (WO) .
9522591 8/1995 (WO) .

OTHER PUBLICATIONS

Pickel, K.H., et al., "Supercritical fluids solvents for reactions", Proceedings of the 3rd International Symposium on Supercritical Fluids, Oct. 17–19, 1994, Strasburg, France, International Society for the Advancement of Supercritical Fluids, Tome 3, pp. 25–29.

Pickel et al. "Supercitical Fluid Sovents for Reactions", *Proc. 3rd Int'l Symp. on Supercritical Fluids* pp 25–29 (1994).

*Primary Examiner*—Deborah D. Carr
(74) *Attorney, Agent, or Firm*—Oppedahl & Larson LLP

(57) ABSTRACT

A partially hydrogenated fatty substance produced by partial hydrogenation of a substrate, such as vegetable, animal or marine oil, said partially hydrogenated substance having a low content of trans fatty acids. When the hydrogenation degree is below 30% the trans-fatty acid concentration can be expressed in the following way: trans≦0.3×(initial IV—IV) in %. of the total amount of fatty acids, wherein IV refers to iodine value. When the hydrogenation degree is between 30 and 70% the trans-fatty acid concentration can be expressed with: trans≦0.09×initial IV in % of the total amount of fatty acids. The partial hydrogenation is performed by a process in which the substrate, hydrogen gas and a solvent are mixed, and the whole mixture is brought into a supercritical or near-critical state. This substantially homogeneous super-critical or near-critical solution is led over the catalyst, whereby the reaction products formed, i.e. the hydrogenated substrates, will also be a part of the substantially homogeneous super-critical or near-critical solution.

6 Claims, 1 Drawing Sheet

PARTIALLY HYDROGENATED FATTY SUBSTANCES WITH A LOW CONTENT OF TRANS FATTY ACIDS

This application is a continuation-in-part of the U.S. patent application Ser. No. 08/765,622, filed Dec. 27, 1996, now U.S. Pat. No. 5,962,711, which is incorporated herein by reference and which is a national phase application under section 371 based upon PCT/SE95/00824, filed Jul. 3, 1995.

TECHNICAL FIELD OF THE INVENTION

The present invention relates to partially hydrogenated fatty substances produced by partial hydrogenation of a substrate, such as vegetable, animal or marine oil. The hydrogenation is performed by a process, in which hydrogen gas is mixed with the substrate in the presence of a catalyst and the reaction is carried out at certain reaction conditions of pressure, time and temperature. The hydrogenation reactions are mainly related to the hydrogenation of carbon-carbon double bonds (C═C) in lipids.

BACKGROUND OF INVENTION

C═C in lipids.

The annual production of vegetable oils is about 90.million toils (Mielke 1992), of which about 20% are hardened (hydrogenated). Furthermore, about 2 million tons of marine oils are hydrogenated yearly. The production is spread over the whole industrialized world. Through the hydrogenation, hydrogen is added to the double bonds of the unsaturated fatty acids. The largest part of the oils is only partly hydrogenated. The desired conditions of melting and the desired consistency of the fats are thereby obtained, which are of importance for the production of margarine and shortening. The tendency to oxidation is reduced by the hydrogenation, and the stability of the fats is increased at the same time (Swern 1982).

In the future, the lipids may be modified by methods belonging to biotechnology, especially gene technology, but hydrogenation will certainly remain.

A problem with the hydrogenation processes of today is, that new fatty acids are produced which to a great extent do not exist in the nature. They are often called trans fatty acids, but the double bonds change position as well as form (cis-trans) during the hydrogenation (Allen 1956, Allen 1986).

Natural fats and oils contain cis double bonds almost exclusively. As a cis double bond is activated at the catalyst surface, it may:

(1) saturate, provided two activated hydrogen atoms are available at a distance sufficiently small, or (2) deactivate and reform the double bond. However, in reforming trans and cis are created at a ratio of about 3.1.

Thus the formation of trans fatty acids is the result of activated hydrogen not being sufficiently available.

In the beginning of a hydrogenation trans fatty acids are only formed, as it proceeds trans fatty acids are being saturated in parallel to the cis double bonds. The saturation of the latter is preferred and in the equilibrium the ratio of trans to cis is about 2:1.

It follows that the amount of trans fatty acids generate a maximum; at the beginning and at the end of the hydrogenation process it is zero. The size of the maximum depends on and increases with two parameters.

(1) the span of hydrogenation possible, i e the initial iodine value (IV), and (2) the rate of formation of trans fatty acids in the reactor.

As a rule, trans fatty acids are desired from a technical and functional point of view (Swern 1982), but regarding health, their role is becoming more and more questionable (Wahle & James 1993).

A typical state of the art reactor for hydrogenation is a large tank (5 to 20 $m^3$) filled with oil and hydrogen gas plus a catalyst in the form of fine particles (nickel in powdery form). The reaction is carried out at a low pressure, just above atmospheric (0,5 to 5 bar), and high temperatures (130 to 210° C.). The hydrogen gas is thoroughly mixed into the oil, as this step restricts the reaction rate (Grau et al., 1988).

If the pressure of hydrogen gas is increased from 3 to 50 bar when soya oil is partially hydrogenated (iodine number at the start=135, at the end=70), the content of trans is reduced from 40 to 15%. The position isomerization is also reduced to a corresponding level (Hsu et al., 1989). These results are of no commercial interest, as these conditions enforce a replacement of the low pressure autoclaves by high pressure autoclaves.

According to the "half hydrogenation" theory, the concentration of activated H-atoms on the catalyst surface determines the number of double bonds being hydrogenated and deactivated without being hydrogenated respectively. A lack of activated H-atoms causes a trans- and position-isomerization (Allen 1956, Allen 1986). A lack of activated H-atoms can be the consequence of low solubility of $H_2$ in the oil, or of a bad catalyst (poisoned or inadequately produced). Thus, the "half hydrogenation" theory corresponds very well to the empirical results (Allen 1956; Allen 1986; Hsu et al., 1989).

It is possible to deodorize and hydrogenate an oil in the presence of $CO_2$ and hydrogen (Zosel 1976). Zosel describes in detail how to use $CO_2$ in order to deodorize the oil. However, it must be emphasized that Zosel does not give any hint, that $CO_2$ should have an influence on the hydrogenation process. Furthermore, Zosel does not touch on the cis/trans problem.

In the experiments of Zosel, the catalyst is surrounded by a liquid phase during the entire process. Zosel does not disclose the composition, but in the light of the other data, we estimate that the liquid phase consists of oil (about 95%), $CO_2$ (about 5%) and hydrogen (about 0.03%). This phase is far away from a supercritical condition. As a consequence, the velocity of reaction is limited by the concentration of hydrogen on the catalyst surface. The same applies to all traditional hydrogenation reactions where the catalyst is in the liquid phase as well. The velocity of hydrogenation in the experiments of Zosel is about 100 kg/$m^3$h, i.e. somewhat lower than in traditional hydrogenation reactors.

THE OBJECT OF THE INVENTION AND MOST IMPORTANT CHARACTERISTICS

The object of the present invention is to obtain a partially hydrogenated fatty substance produced by partial hydrogenation of a substrate, such as vegetable, animal or marine oil which has a very low content of trans fatty acids.

When the hydrogenation degree is below 30% the trans-fatty acid concentration can be expressed in the following way: trans$\leqq$0.3×(initial IV–IV)%. When the hydrogenation degree is between 30 and 70% the trans-fatty acid concentration can be expressed with: trans$\leqq$0.09×initial IV %.

IV here refers to the iodine value.

Such low contents of trans fatty acids is obtained by a very effective hydrogenation process which is performed by mixing the substrate, hydrogen gas and solvent, and by bringing the whole mixture into a super-critical or near-critical state. This substantially homogeneous super-critical or near-critical solution is led over the catalyst, whereby the reaction products formed, i.e. the hydrogenated substrates, will also be a part of the substantially homogeneous super-critical or near-critical solution. At partial hydrogenation the reaction is interrupted at a certain iodine value (IV).

The determining factor of the present invention is that by making hydrogen available ad libitum at the catalyst surface, preference is given to the reaction of saturation of the cis double bonds and not to the reaction of deactivation and reformation of the double bonds to trans bonds.

The solvent can be a saturated hydrocarbon or an unsaturated hydrocarbon which on hydrogenation gives a saturated hydrocarbon, e.g. ethane, ethene, propane, propene, butane, butene, or $CO_2$, dimethyl ether, "freons", $N_2O$, $N_2$, $NH_3$, or mixtures thereof.

Propane is a suitable solvent for many lipids.

The catalyst will be selected according to the reaction which is to be carried out. For a partial or complete hydrogenation of only C═C bonds, preferably a noble metal or nickel will be selected. For a selective hydrogenation of COOR to C—OH and HO—R, the catalyst would preferably be a zinc salt, e.g. zinc chromite. For a simultaneous hydrogenation of COOR to C—OH and HO—R and a hydrogenation of C═C, the preferred catalyst would be copper chromite, another salt of copper or copper free from chrome.

According to the invention, the concentration of hydrogen on the catalyst surface can be controlled to very high levels. The proportion of trans fatty acids in partially hydrogenated fatty products will be much lower according to the invention than by using conventional processes, where the product has been hydrogenated to the same level using the same catalyst.

DESCRIPTION OF THE INVENTION

Figure 1:
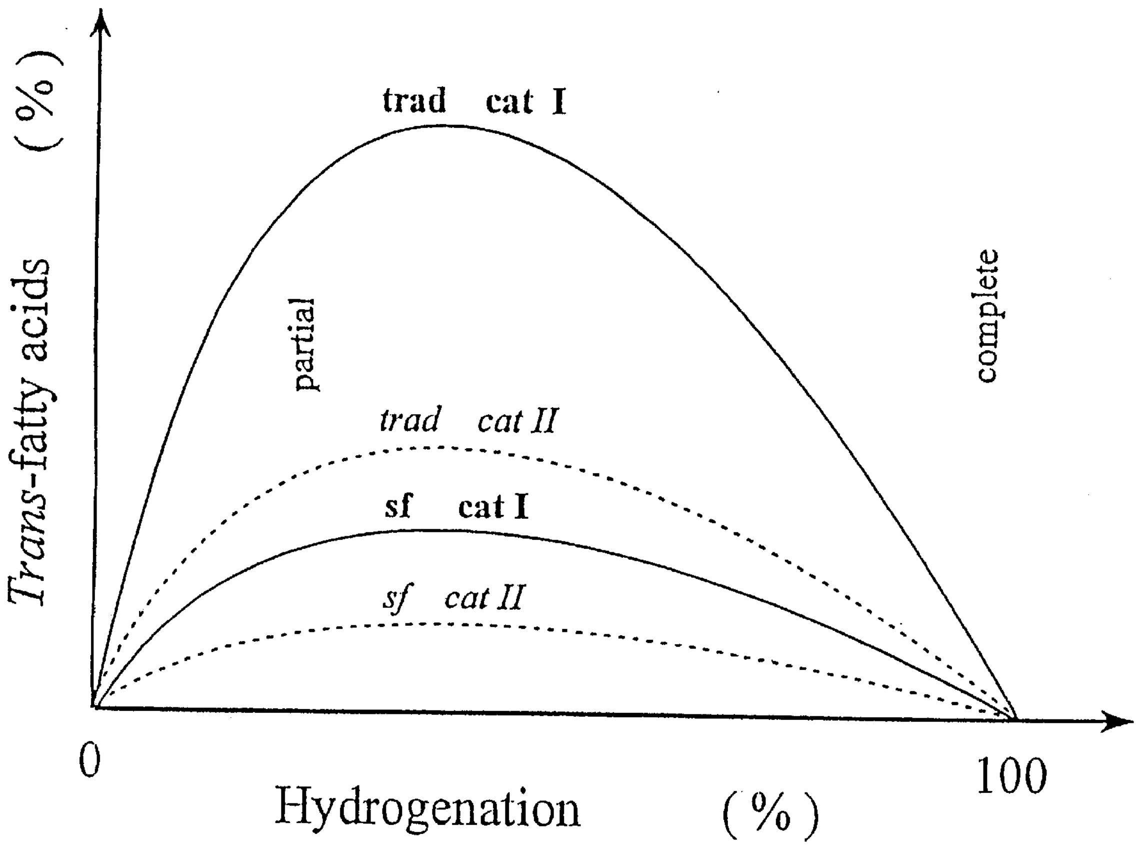
FIG. 1 is a diagram showing the percentage of trans fatty acids as a function of the degree of hydrogenation according to a traditional technique and according to the invention.

The Problem.

In a great number of hydrogenation processes, hydrogen gas is mixed with a liquid substrate and a fixed catalyst, e.g. in the hydrogenation of lipids. In certain cases the substrate can be a gas and the product a liquid, e. g. hydrogenation of oxygen to hydrogen peroxide and water. In both these cases, the velocity of reaction is limited by the concentration of gas on the catalyst surface. The reason is the transport resistances of the gas: between the gas phase and the liquid phase; through the liquid phase; and between the liquid phase and the catalyst.

THE SUBJECT MATTER OF THE INVENTION

The idea is to add a solvent, which completely dissolves the gas as well as the liquid, resulting in a substantially homogeneous mixture of hydrogen, substrate, product and solvent. This is possible, if the whole mixture is in a super-critical or near-critical state. The definition substantially homogeneous means, that the principal part of the gas is in the continuous phase which covers the catalyst surface. One method to confirm this is to observe the velocity of reaction, which increases dramatically when the continuous phase that covers the catalyst surface is substantially homogeneous.

VELOCITY OF REACTION

According to the invention, the following transport resistances of the gas are reduced substantially: gas phase/liquid phase; through the liquid phase; and liquid phase/catalyst. The velocity of reaction thereby increases to a very high degree; from about 10 to about 1000 times. The consequence of this is that continuous reactors will be preferred compared to the batch reactors of today. The selectivity is also influenced to a very high degree.

SOLVENT

In order to bring the whole mixture (hydrogen, substrate, product and solvent) to super critical or near-critical state at appropriate pressures and temperatures, the solvent must dissolve substrate and product as much as possible.

Glycerides, fatty acids and many derivatives of fatty acids are completely miscible with supercritical propane (Peter et al.,1993). Propane can be used in any proportions together with food according to EU-regulations (Sanders 1993; EC 1984). Thus, propane is a very adequate solvent in reactions with lipids.

CATALYSTS

The catalysts which are used today in traditional processes can in principle also be used in super-critical processes. The catalyst may however be modified to optimize selectivity, velocity of reaction, length of life, filtering properties and pressure-drop.

QUALITY OF PRODUCT

The invention enables new possibilities to control the hydrogen concentration at the catalyst. The velocity of reaction increases substantially. The selectivity can also be influenced in certain processes. By partial hydrogenation of edible oils, the content of trans fatty acids is of importance for the quality (see background of invention).

Different substrates have different concentrations of double bonds. Traditionally, this property is expressed by an iodine value (IV), e.g. palm oil has an IV of about 50, rapeseed oil has an IV of about 115, sunflower oil has an IV of about 130, soya oil has an IV of 135 and fish oil has an IV ranging from 115 to about 200. During hydrogenation the content of double bonds decreases.

In FIG. 1 we describe the formation of trans fatty acids in different hydrogenation processes. On the x-axis we write hydrogenation in %, i.e. IVchange/Ivinitial·100. A hydrogenation degree of 50% for a substrate having an IVinitial of 130 means that the IV has reached 65. In all hydrogenation processes the content of trans-fatty acids increase from zero through a maximum at a hydrogenation degree between 30 and 70%, and at full hydrogenation the trans content returns to zero.

FIG. 1 also illustrates in principle how the proportion of trans fatty acids changes during hydrogenation with two different catalysts, one catalyst according to a traditional technique and another according to the new super-critical technique. The new supercritical technique makes it possible to reduce the content of trans fatty acids in comparison with the traditional technique using the same catalyst and the same degree of hydrogenation. However, using different catalysts, the difference may be less, see FIG. 1.(In FIG. 1, "trad" means traditional process; "sf" means process with super critical fluid; and "cat" means catalyst.)

CONDITIONS OF REACTION

C═C in lipids.

I. Partial Hydrogenation.

At partial hydrogenation, the reaction is interrupted at a certain iodine value. The substrate, e.g. vegetable, animal or marine oil, and hydrogen are dissolved in a solvent, e.g. propane. The mixture is brought to a supercritical or a near-critical state. The substantially homogeneous mixture is brought into contact with a catalyst, e.g. palladium.

A general relation between the content of traps fatty acids during a hydrogenation process is described in FIG. 1. We can see that the trans content is always lower when the catalyst is in contact with a substantially homogeneous mixture. The trans fatty acid concentration during the initial stage and at the maximum level during the new hydrogenation process are defined below.

When a good catalyst is used in combination with a substantially homogeneous mixture and the hydrogenation degree is below 30% the trans-fatty acid concentration can be expressed in the following way: trans≦0.3×(initial IV—IV) %. This means that if the substrate has an initial IV of 115 and the IV is in the range from 115 to 80 the maximal trans fatty acid concentration is no more than [0.3×(115–IV)]%.

When a good catalyst is used in combination with a substantially homogeneous mixture, the maximal content of trans fatty acids during a hydrogenation process is no more than 9% of the initial IV for the substrate. This means that if the substrate has an initial IV of 115 the maximal content of trans fatty acids in a partially hydrogenated product is no more than 0.09×115=10% of the total amount of fatty acids. This maximal trans content occures when the IV is the range of 30 to 70% of 115, i.e. at IV in the range of 80 to 35.

The optimal reaction condition may occure over a wide experimental range and this range can be described as follows:

| | in general | preferably |
|---|---|---|
| temperature | 0–250° C. | 20–200° C. |
| pressure | 10–350 bar | 20–200 bar |
| time of reaction | 0*–10 min | 1 μsec–1 min |
| solvent | 30–99,9 wt % | 40–99 wt % |

The solvent must dissolve the substrates at the concentrations used. The solvent can be ethane, ethene, propane, propene, butane, butene, $CO_2$, dimethyl ether, "freons", $N_2O$, $N_2$, $NH_3$ or mixtures of these gases. Preferred are propane, propene, butane, butene and dimethyl ether. Most preferred is propane.

| | | |
|---|---|---|
| concentration of $H_2$ | 0*–3 wt % | 0,001–1 wt % |
| concentration substrate | 0,1–70 wt % | 1–60 wt % |
| type of substrate: | | |

C═C in general. Glycerides are preferred (mono-, di-, triglycerides,

-continued galactolipids, phospholipids), also fatty acids or their derivatives (e.g. methyl- and ethyl-esters).
catalysts
noble metals: Pd, Pt, Os, . . . but also Ni.

(0* means very low values, below the lowest one under "preferably").

II. Complete Hydrogenation.

At complete hydrogenation, all double bonds are hydrogenated and the iodine number is therefore near zero. The substrate, e.g. vegetable, animal or marine oil, and hydrogen are dissolved in a solvent, e.g. propane. The mixture is brought to a supercritical or near-critical condition, and the substantially homogeneous mixture is brought into contact with a catalyst, e.g. palladium.

The optimal conditions of reaction are wide and can be described in a similar way as for partial hydrogenation; the temperature is, however, somewhat higher than for partial hydrogenation (T is probably higher than $T_{crit}$).

EQUIPMENT AND ANALYTICAL METHODS

Equipment

Figure 2:
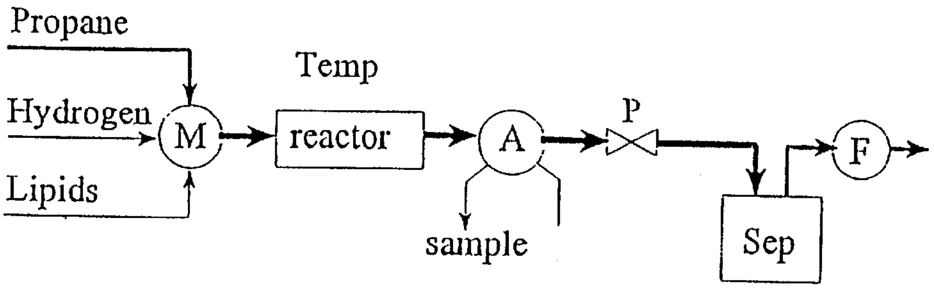
FIG. 2 is a flow sheet for a process according to the invention.

A flow sheet for the continuous reactor used, is illustrated in FIG. 2. In this figure "M" is a mixer, "Temp." a temperature controller, "A" a sampling device for analyses, "P" a pressure reduction valve, "Sep" a vessel for separation of gas/liquids and "F" a gas flow-meter. At room temperature a condensed gas, a non-condensable gas and a liquid were mixed according to the principles used by Pickel in a "Supercritical Fluid Chromatography" application (Pickel 1991). Pickel mixed $CO_2$ nitrogen and a liquid entrainer. We mixed propane (1), hydrogen (g) and lipids (see M in FIG. 2). The same equipment can be used for the hydrogen peroxide experiments but in this case one add: $CO_2$ (1); oxygen+hydrogen (g); reaction aids (1).

The mixture was heated to the desired reaction temperature and was brought into an HPLC tube filled with a catalyst powder (see Temp and Reactor in FIG. 2).

After the reactor samples were collected from the high pressure section using an HPLC valve (see A in FIG. 2 and Härröd et al 1994). The pressure was reduced to atmospheric pressure and lipids and gases were separated (see P and Sep in FIG. 2). Then the gas flow was measured (see F in FIG. 2) The gasflow was controlled by the pressure-reduction valve (P in FIG. 2).

Analysis

The product quality was analysed using silver-ion-HPLC and gradient elution (Elfman Härröd 1995). This method is developed from an isocratic method (Adolf 1994). The kind (cis/trans) and the amount of the fatty acid methyl esters (FAME) was determine. From these data the iodine value (IV) was calculated.

The density was calculated from the Peng-Robinsson equation of state (Dohrn 1994).

EXAMPLES

Example 1

Partial Hydrogenation of Methyl Esters From Rapeseed Oil Using a Palladium Catalyst Composition and Amound of the Inlet Flow to the Reactor:

| | mole % | weight % | mg/min |
|---|---|---|---|
| propane | 99.92 | 99.7 | 3700 |
| hydrogen | 0.04 | 0.002 | 0.07 |
| FAME | 0.04 | 0.26 | 10 |

Reaction Conditions:

| | |
|---|---|
| catalyst | 5% Pd on char coal (E 101 O/D 5% Degussa AG) |
| reactor volume | 0,007 ml |
| reaction time | 40 ms |
| temperature | 50° C. |
| pressure | 120 bar |

Productivity and Product Quality:

| | |
|---|---|
| productivity | 80 000 kg FAME/$m^3$ h |
| Iodine-value | reactor inlet = 110 |
| | reactor outlet = 50 |
| FAME with trans | 10% of all FAME; <9% · IV at inlet |

Comments

This example shows that a very high productivity (80 000 kg FAME/$m^3$ h) and a low content of trans-fatty acids (10% of all FAME or expressed as <9%·IV at inlet) can be attained at near-critical conditions. The results above is only an example. We do not claim that it is the optimal conditions for the process. Others (Berben et al 1995) has minimized the trans-fatty acid content using the conventional technique. The productivity became much lower (700 kg triglycerides/$m^3$ h) and the content of the trans-fatty acids became much higher (34%).

Example 2

Complete Hydrogenation of Methylesters From Rapeseed Oil Using a Palladium Catalyst Composition and Amount of the Inlet Flow to the Reactor:

| | mole % | weight % | mg/min |
|---|---|---|---|
| propane | 96.27 | 95.7 | 1840 |
| hydrogen | 3.1 | 0.14 | 2.7 |
| FAME | 0.63 | 4.16 | 80 |

Reaction Conditions:

| | |
|---|---|
| catalyst | 504 Pd on char coal (E101 O/D 5% Degussa AG) |
| reactor volume | 0.007 ml |
| reaction time | 80 ms |
| temperature | 90° C. |
| pressure | 70 bar |

Productivity and Product Quality:

| | |
|---|---|
| productivity | 700 000 kg FAME/$m^3$h |
| Iodine-value | reactor inlet = 110 |
| | reactor outlet < 1 |
| FAME with trans | <0.1% of all FAME |

Comments

This example shows that a tremendous productivity (700 000 kg FAME/$m^3$ h) can be attained at near-critical conditions. The results above is only an example. We do not claim that it is the optimal conditions for the process.

Example 3

Complete Hydrogenation of Methylesters From Rapeseed Oil Using a Nickel Catalyst Composition and Amount of the Inlet Flow to the Reactor:

| | mole % | weight % | mg/min |
|---|---|---|---|
| propane | 99.49 | 99.13 | 1500 |
| hydrogen | 0.38 | 0.017 | 0.25 |
| FAME | 0.13 | 0.85 | 13 |

Reaction Conditions:

| | |
|---|---|
| catalyst | Nickel (Ni-5256 P, Engelhard) |
| reactor volume | 0.009 ml |
| reaction time | 65 ms |
| temperature | 190° C. |
| pressure | 155 bar |

Productivity and Product Quality:

| | |
|---|---|
| productivity | 90 000 kg FAME/$m^3$ h |
| Iodine-value | reactor inlet = 110 |
| | reactor outlet < 1 |
| FAME with trans | <0.1% of all FAME |

Comments

This example shows that a very high productivity (90 000 kg FAME/$m^3$ h) can be attained using a nickel catalyst at super-critical conditions. The results above is only an example. We do not claim that it is the optimal conditions for the process.

Example 4

Complete Hydrogenation of Triglycerides Using a Palladium Catalyst

Composition and Amount of the Inlet Flow to the Reactor:

| | mole % | weight % | mg/min |
|---|---|---|---|
| propane | 98.7 | 93.6 | 3600 |
| hydrogen | 1 | 0.043 | 1.6 |
| triglycerides | 0.3 | 6.3 | 240 |

The triglycerides (tg) were in this case a commeicial vegetable oil.

Reaction Conditions:

| | |
|---|---|
| catalyst | 5% Pd on char coal (E 101 O/D 5% Degussa AG) |
| reactor volume | 2.5 ml |
| reactor time | 12 sec |
| temperature | 50° C. |
| pressure | 100 bar |

Productivity and Product Quality:

| | |
|---|---|
| productivity | 5 000 kg tg/$m^3$ h |
| Iodine-value | reactor inlet = 140 |
| | reactor outlet = 0.1 |
| FA with trans | <0.1% of all FA |

Comments:

This example shows that a high productivity (5000 kg triglycerides/$m^3$ h) can be attained at near-critical conditions. The results above is only an example. We do not claim that it is the optimal conditions for the process.

What is claimed is:

1. A partially hydrogenated fatty substance produced by partial hydrogenation of a substrate having an initial iodine value (initial IV), said partially hydrogenated fatty substance being hydrogenated to a hydrogenation degree of below 30% and having an iodine value (IV), wherein the partially hydrogenated fatty substance has a content of trans fatty acids of no more than 0.3×(initial IV—IV) in % of the total amount of fatty acids.

2. A partially hydrogenated fatty substance as claimed in claim 1, wherein the content of trans fatty acids is no more than 0.2×(initial IV–IV) in % of the total amount of fatty acids.

3. The partially hydrogenated fatty substance of claim 1, wherein the substrate is vegetable, animal or marine oil.

4. A partially hydrogenated fatty substance produced by partial hydrogenation of a substrate, said partially hydrogenated substance being hydrogenated to a hydrogenation degree of between 30 and 70% and having a content of trans fatty acids of no more than 0.09×initial IV in % of the total amount of fatty acids.

5. A partially hydrogenated fatty substance as claimed in claim 4, wherein the content of trans fatty acids is no more than 0.05×initial IV in % of the total amount of fatty acids.

6. The partially hydrogenated fatty substance of claim 4, wherein the substrate is vegetable, animal or marine oil.

* * * * *